US007505902B2

(12) United States Patent
Mesgarani et al.

(10) Patent No.: US 7,505,902 B2
(45) Date of Patent: Mar. 17, 2009

(54) DISCRIMINATION OF COMPONENTS OF AUDIO SIGNALS BASED ON MULTISCALE SPECTRO-TEMPORAL MODULATIONS

(75) Inventors: Nima Mesgarani, College Park, MD (US); Shihab A. Shamma, Washington, DC (US)

(73) Assignee: University of Maryland, College Park, MD (US)

( * ) Notice: Subject to any disclaimer, the term of this patent is extended or adjusted under 35 U.S.C. 154(b) by 599 days.

(21) Appl. No.: 11/190,933

(22) Filed: Jul. 28, 2005

(65) Prior Publication Data

US 2006/0025989 A1 Feb. 2, 2006

Related U.S. Application Data

(60) Provisional application No. 60/591,891, filed on Jul. 28, 2004.

(51) Int. Cl.

*G10L 11/00* (2006.01)
*G10L 11/02* (2006.01)
*G10L 21/06* (2006.01)
*G10L 15/08* (2006.01)
*A61B 5/00* (2006.01)

(52) U.S. Cl. ....................... 704/231; 704/205; 704/206; 704/233; 704/235; 600/301

(58) Field of Classification Search ...... 704/200–200.1, 704/204, 205–206, 207, 229, 231–257, 220–228, 704/500–504; 381/110; 600/300–301, 372, 600/379, 382–383
See application file for complete search history.

(56) References Cited

U.S. PATENT DOCUMENTS 4,718,094 A * 1/1988 Bahl et al. .................. 704/256
4,843,562 A * 6/1989 Kenyon et al. ................ 702/73
5,040,217 A * 8/1991 Brandenburg et al. ..... 704/200.1
5,247,436 A * 9/1993 Stone, Jr. ..................... 600/372
5,320,109 A * 6/1994 Chamoun et al. ........... 600/544
6,308,155 B1 * 10/2001 Kingsbury et al. ....... 704/256.1
6,363,345 B1 * 3/2002 Marash et al. ............. 704/226
6,570,991 B1 * 5/2003 Scheirer et al. ............. 381/110
7,117,149 B1 * 10/2006 Zakarauskas .............. 704/233
7,191,128 B2 * 3/2007 Sall et al. .................... 704/233
7,254,535 B2 * 8/2007 Kushner et al. ............. 704/226
7,295,977 B2 * 11/2007 Whitman et al. ............ 704/236
2001/0044719 A1 * 11/2001 Casey ......................... 704/245
2001/0049480 A1 * 12/2001 John et al. .................. 600/559
2004/0260540 A1 * 12/2004 Zhang ......................... 704/205
2005/0222840 A1 * 10/2005 Smaragdis .................. 704/204
2008/0147402 A1 * 6/2008 Jeon et al. ................... 704/251

OTHER PUBLICATIONS

Fineberg et al., "Detection and Classification of Multicomponent Signals", 1991 Conference Record of the Twenty-Fifth Asilomar Conference on Signals, Systems and Computers, Nov. 4-6, 1991, vol. 2, 1093-1097.*

(Continued)

*Primary Examiner*—Talivaldis I Smits
*Assistant Examiner*—David Kovacek
(74) *Attorney, Agent, or Firm*—Rosenberg, Klein & Lee

(57) ABSTRACT

An audio signal (172) representative of an acoustic signal is provided to an auditory model (105). The auditory model (105) produces a high-dimensional feature set based on physiological responses, as simulated by the auditory model (105), to the acoustic signal. A multidimensional analyzer (106) orthogonalizes and truncates the feature set based on contributions by components of the orthogonal set to a cortical representation of the acoustic signal. The truncated feature set is then provided to classifier (108), where a predetermined sound is discriminated from the acoustic signal.

20 Claims, 12 Drawing Sheets

OTHER PUBLICATIONS

De Lathauwer et al., "On the Best Rank-1 and Rank—(R1, R2, . . . RN) Approximation of Higher Order Tensors", Siam J. of Matrix Anal. and App., vol. 21, No. 4, 2000.

Kingsbury et al., "Robust Speech Recognition in Noisy Environments: The 2001 IBM Spine Evaluation System", Int'l Conf. on Acoustic, Speech and Signal Proc., vol. I, Orlando, Fla., May 2002.

Scheirer, et al., "Construction and Evaluation of a Robust Multifeature Speech/Music Discriminator", Int'l Conf. on Acoustic, Speech and Signal Proc., Munich, Germany, 1997.

* cited by examiner

DISCRIMINATION OF COMPONENTS OF AUDIO SIGNALS BASED ON MULTISCALE SPECTRO-TEMPORAL MODULATIONS

RELATED APPLICATION DATA

This application is based on Provisional Patent Application Ser. No. 60/591,891, filed 28 Jul. 2004.

STATEMENT REGARDING FEDERALLY SPONSORED RESEARCH

The invention described herein was developed through research funded under Federal contract. The U.S. Government has certain rights to the invention.

BACKGROUND OF THE INVENTION

1. Field of the Invention

The invention described herein is related to discrimination of a sound from components of an audio signal. More specifically, the invention is directed to analyzing a modeled response to an acoustic signal for purposes of classifying the sound components thereof, reducing the dimensions of the modeled response and then classifying the sound using the reduced data.

2. Description of the Prior Art

Audio segmentation and classification have important applications in audio data retrieval, archive management, modern human-computer interfaces, and in entertainment and security tasks. Manual segmentation of audio sounds is often difficult and impractical and much emphasis has been given recently to the development of robust automated procedures.

In speech recognition systems, for example, discrimination of human speech from other sounds that co-occupy the surrounding environment is essential for isolating the speech component for subsequent classification. Speech discrimination is also useful in coding or telecommunication applications where non-speech sounds are not the audio components of interest. In such systems, bandwidth may be better utilized when the non-speech portion of an audio signal is excluded from the transmitted signal or when the non-speech components are assigned a low resolution code.

Speech is composed of sequences of consonants and vowels, non-harmonic and harmonic sounds, and natural silences between words and phonemes. Discriminating speech from non-speech is often complicated by the similarity of many sounds, such as animal vocalizations, to speech. As with other pattern recognition tasks, the first step in any audio classification is to extract and represent the sound by its relevant features. Thus, the need has been felt for a sound discrimination system that generalizes well to particular sounds, and that forms a representation of the sound that both captures the discriminative properties of the sound and resists distortion under varying conditions of noise.

SUMMARY OF THE INVENTION

In a first aspect of the present invention, a method for discriminating sounds in an audio signal is provided which first forms from the audio signal an auditory spectrogram characterizing a physiological response to sound represented by the audio signal. The auditory spectrogram is then filtered into a plurality of multidimensional cortical response signals, each of which is indicative of frequency modulation of the auditory spectrogram over a corresponding predetermined range of scales (in cycles per octave) and of temporal modulation of the auditory spectrogram over a corresponding predetermined range of rates (in Hertz). The cortical response signals are decomposed into multidimensional orthogonal component signals, which are truncated and then classified to discriminate therefrom a signal corresponding to a predetermined sound.

In another aspect of the present invention, a method is provided for discriminating sounds in an acoustic signal. A known audio signal associated with a known sound having a known sound classification is provided and a training auditory spectrogram is formed therefrom. The training spectrogram is filtered into a plurality of multidimensional training cortical response signals, each of which is indicative of frequency modulation of the training auditory spectrogram over a corresponding predetermined range of scales and of temporal modulation of the training auditory spectrogram over a corresponding predetermined range of rates. The training cortical response signals are decomposed into multi-dimensional orthogonal component training signals and a signal size corresponding to each of said orthogonal component training signals is determined. The signal size sets a size of the corresponding orthogonal component training signal to retain for classification. The orthogonal component training signals are truncated to the signal size and the truncated training signals are classified. The classification of the truncated component training signals are compared with a classification of the known sound and the signal size is increased if the classification of the truncated component training signals does not match the classification of the known sound to within a predetermined tolerance.

Once the signal size has been set, the acoustic signal is converted to an audio signal and an auditory spectrogram therefrom. The auditory spectrogram is filtered into a plurality of multidimensional cortical response signals, which are decomposed into orthogonal component signals. The orthogonal component signals are truncated to the signal size and classified to discriminate therefrom a signal corresponding to a predetermined sound.

In yet another aspect of the invention, a system is provided to discriminate sounds in an acoustic signal. The system includes an early auditory model execution unit operable to produce at an output thereof an auditory spectrogram of an audio signal provided as an input thereto, where the audio signal is a representation of the acoustic signal. The system further includes a cortical model execution unit coupled to the output of the auditory model execution unit so as to receive the auditory spectrogram and to produce therefrom at an output thereof a time-varying signal representative of a cortical response to the acoustic signal. A multi-linear analyzer is coupled to the output of the cortical model execution unit, which is operable to determine a set of multi-linear orthogonal axes from the cortical representations. The multi-linear analyzer is further operable to produce a reduced data set relative to the set of orthogonal axes. The system includes a classifier for determining speech from the reduced data set.

DETAILED DESCRIPTION OF PREFERRED EMBODIMENTS

Figure 1:
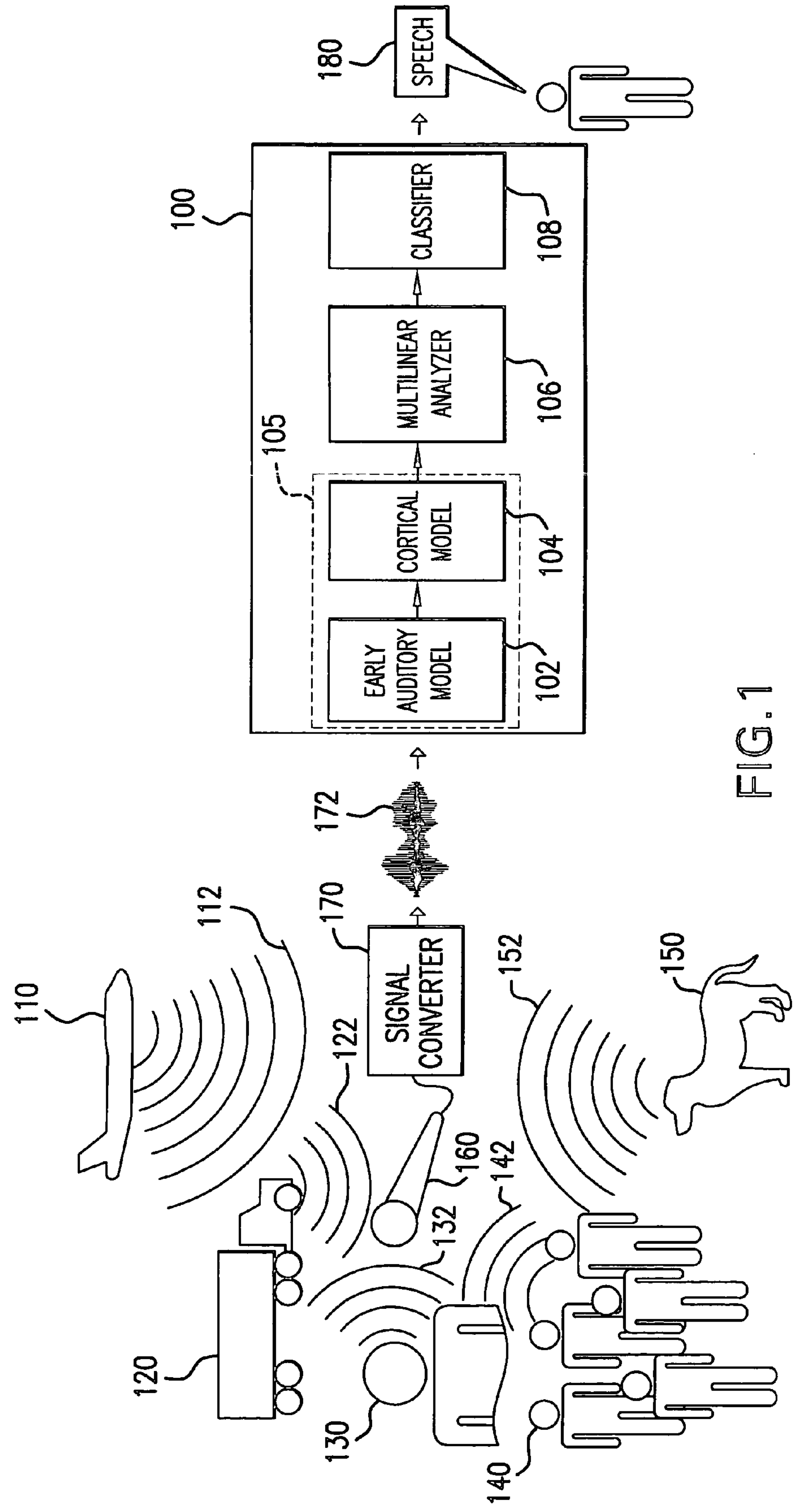
FIG. 1 is a block diagram of an exemplary embodiment of a system operable in accordance with the present invention.

Referring to FIG. 1, there is shown in broad overview an exemplary embodiment of the present invention. As is shown in the Figure, several sources of acoustic energy distributed in a region of space are generating a combined acoustic signal having several components. To illustrate aspects of the invention, it will be assumed, merely for purposes of illustration, that human speech 132 emitted by user 130 is the acoustic signal of interest. The speech signal 132 is a component of the overall acoustic signal, which includes jet engine noise 112 from aircraft 110, traffic noise 122 emanating from automotive traffic 120, crowd noise 142 from surrounding groups of people 140 and animal noises 152 emitted by various animals 150. In the illustrated example, it is desired to discriminate the human speech 132 from the other sounds, however, it is to made clear that the present invention is not limited to such application. Discrimination of any sound is possible with the invention by implementing an appropriate classifier, which is discussed further below.

As is known in the art, an acoustic signal may be converted into a representative signal thereof by employing the appropriate converting technologies. In the exemplary embodiment of FIG. 1, the acoustic energy of all sources is incident on a transducer, indicated by microphone 160, and is converted to an audio signal 172 by signal converter 170. As used herein, an acoustic signal, which is characterized by oscillations in the material of the conveying medium, is distinguished from an audio signal, which is an electrical representation of the acoustic signal. The signal converter 170 may be any device operable to provide the appropriate digital or analog audio signal 172.

Among the beneficial features of the present invention is a feature set characterizing the response of various stages of the auditory system. The features are computed using a model of the auditory cortex that maps a given sound to a high-dimensional representation of its spectro-temporal modulations. The present invention has among its many features an improvement over prior art systems in that it implements a multilinear dimensionality reduction technique, as will be described further below. The dimensional reduction takes advantage of multimodal characteristics of the high-dimensional cortical representation, effectively removing redundancies in the measurements in the subspace characterizing each dimension separately, thereby producing a compact feature vector suitable for classification.

Referring again to FIG. 1, the audio signal is presented to a computational auditory model 105, which simulates neurophysiological, biophysical, and psychoacoustical responses at various stages of the auditory system. The model 105 consists of two basic stages. An early auditory model stage 102 simulates the transformation of the acoustic signal, as represented by the audio signal, into an internal neural representation referred to as an auditory spectrogram. A cortical model stage 104 analyzes the spectrogram to estimate the content of its spectral and temporal modulations using a bank of modulation selective filters that mimics responses of the mammalian primary auditory cortex. The cortical model stage 104 is responsible for extracting the key features upon which the classification is based. As will be described below, the cortical response representations produced by model 105 are presented to multilinear analyzer 106 where the data undergo a reduction in dimension. The dimensionally reduced data are then conveyed to classifier 108 for discriminating the sound of interest from undesired sounds. As previously stated, the example of FIG. 1 is adapted to recognize human speech, so, accordingly, the classifier is trained on known speech signals prior to live analysis. If the system 100 were to be used to discriminate a different sound, for example, the animal sound 152, the classifier 108 would be trained on the appropriate known animal sounds. The desired sound, which in the exemplary embodiment of FIG. 1 is human speech, is then output from the classifier 108, as shown at 180.

Figure 2:
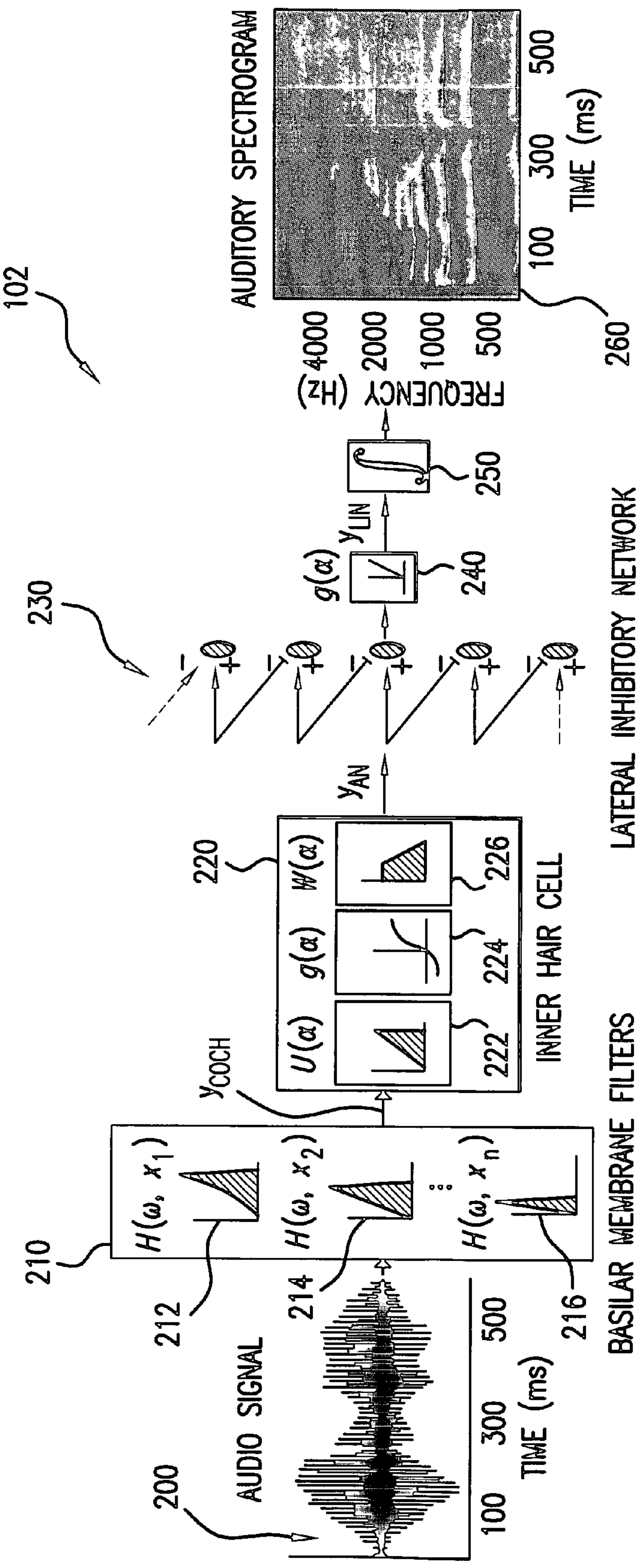
FIG. 2 is a schematic diagram illustrating exemplary system components and processing flow of an early auditory model of the present invention.

An exemplary embodiment of an early auditory model stage 102 consistent with present invention is illustrated in FIG. 2. An acoustic signal entering the ear produces a complex spatio-temporal pattern of vibrations along the basilar membrane of the cochlea. The maximal displacement at each cochlear point corresponds to a distinct tone frequency in the stimulus, creating a tonotopically-ordered response axis along the length of the cochlea. Thus, the basilar membrane can be thought of as a bank of constant-Q highly asymmetric bandpass filters (Q=4) equally spaced on a logarithmic frequency axis. The operation may be considered as an affine wavelet transform of the acoustic signal s(t). The audio signal 200 representing the acoustic signal is introduced to the analysis stage 210, which, in the exemplary embodiment, is implemented by a bank of 128 overlapping constant-Q (QERB=5.88; QERB referring to the bandwidth of a rectangular filter which passes the same amount of energy as the subject filter for white noise inputs) bandpass filters with center frequencies (CF) that are uniformly distributed along a logarithmic frequency axis (f), over 5.3 octaves (24 filters/octave). The frequency response of each filter is denoted by H(ω; x). The cochlear filter outputs $y_{cochlea}(t, f)$, which combined are indicated at $y_{COCH}$ in FIG. 2, are then transformed into auditory-nerve patterns $y_{an}(t; f)$, indicated at $y_{AN}$, by a hair cell stage 220, which converts cochlear outputs into inner hair cell intra-cellular potentials. This process may be modeled as a 3-step operation: a highpass filter 222 (the fluid-cilia coupling), followed by an instantaneous nonlinear compression 224 (gated ionic channels) $g_{hc}(\circ)$, and then a lowpass filter 226 (hair cell membrane leakage), $\mu_{hc}(t)$. Finally, a Lateral Inhibitory Network (LIN) 230 detects discontinuities in the responses across the tonotopic axis of the auditory nerve array. The LIN 230 may be approximated by a first-order derivative with respect to the tonotopic axis and followed by a half-wave rectifier 240 to produce $y_{LIN}(t, f)$. The final output of the early auditory model stage 102 is obtained by integrating $y_{LIN}(t, f)$ via integrator 250 over a short window, $\mu_{midbrain}(t, \tau)$, with time constant τ=8 msec mimicking further loss of phase-locking observed in the midbrain. This stage effectively sharpens the bandwidth of the cochlear filters from about Q=4 to Q=12.

The mathematical formulation for this stage can be summarized as follows:

$$y_{cochlea}(t,f)=s(t)*h_{cochlea}(t;f) \quad (1)$$

$$y_{an}(t,f)=g_{hc}(\partial_t y_{cochlea}(t,f))*\mu_{hc}(t) \quad (2)$$

$$y_{LIN}(t,f)=\max(\partial_f y_{an}(t,f), 0) \quad (3)$$

$$y(t,f)=y_{LIN}(t,f)*\mu_{midbrain}(t;\tau), \quad (4)$$

where * denotes convolution in time.

The exemplary sequence of operations described above computes an auditory spectrogram 260 of the speech signal 200 using a bank of constant-Q filters, each filter having a bandwidth tuning Q of about 12 (or just under 10% of the center frequency of each filter). The auditory spectrogram 260 has encoded thereon all temporal envelope modulations due to interactions between the spectral components that fall within the bandwidth of each filter. The frequencies of these modulations are naturally limited by the maximum bandwidth of the cochlear filters.

Figure 3:
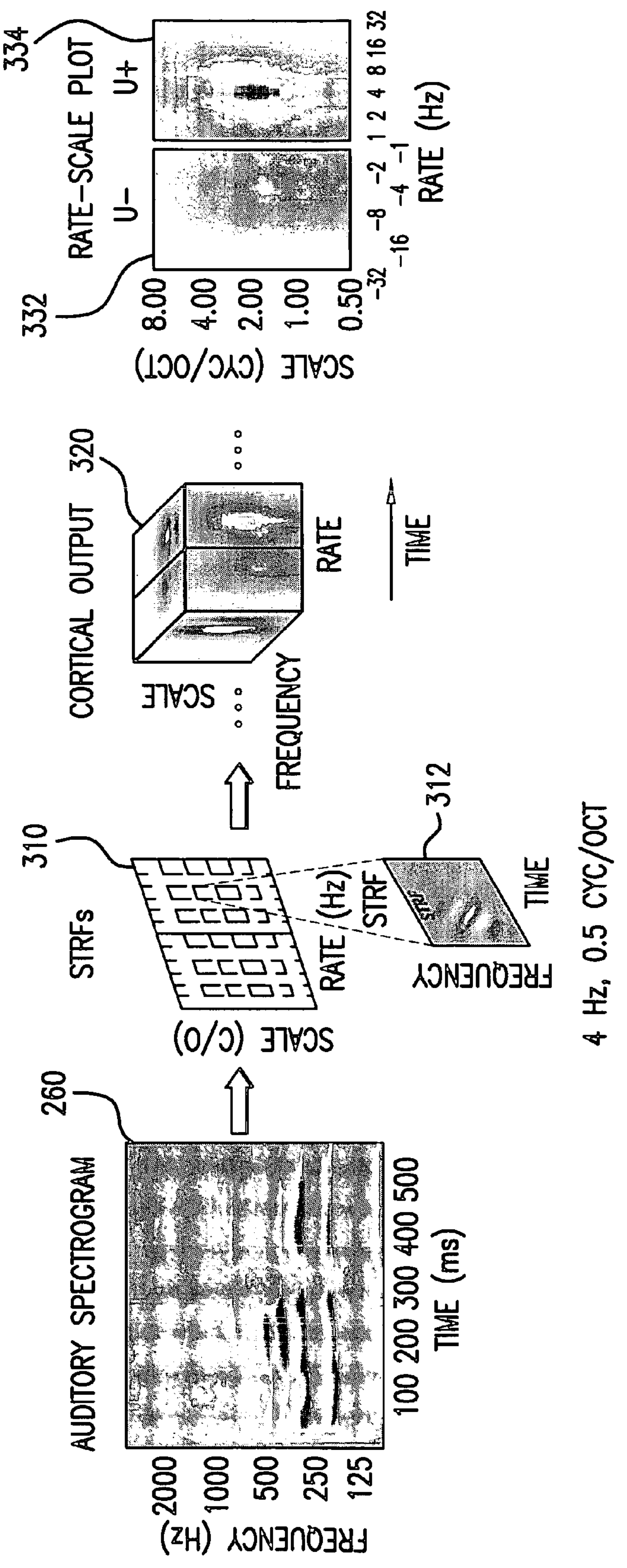
FIG. 3 is a schematic diagram illustrating exemplary system components and processing flow of a cortical model of the present invention.

Higher central auditory stages (especially the primary auditory cortex) further analyze the auditory spectrum into more sophisticated representations, interpret them, and separate the different cues and features associated with different sound percepts. Referring to FIG. 3, there is illustrated an exemplary auditory cortical model 104 operable with the present invention. The exemplary cortical model is mathematically similar to a two-dimensional affine wavelet transform of the auditory spectrogram, with a spectrotemporal mother wavelet resembling a 2-D spectro-temporal Gabor function. Computationally, the cortical model stage 104 estimates the spectral and temporal modulation content of the auditory spectrogram 260 via a bank 310 of modulation-selective filters 312 (the wavelets) centered at each frequency along the tonotopic axis. Each filter 312 is tuned (Q=1) to a range of temporal modulations, also referred to as rates or velocities (ω in Hz) and spectral modulations, also referred to as densities or scales (Ω in cycles/octave). An exemplary Gabor-like spectro-temporal impulse response or wavelet, referred to herein as a Spectro-temporal Response Field (STRF), is illustrated at 312.

In certain embodiments of the present invention, a bank 310 of directional selective STRF's (down-ward [−] and upward [+]) are implemented that are real functions formed by combining two complex functions of time and frequency:

$$STRF_+=\Re\{H_{rate}(t;\omega,\theta)\cdot H_{scale}(f;\Omega,\phi)\} \quad (5)$$

$$STRF_-=\Re\{H^*_{rate}(t;\omega,\theta)\cdot H_{scale}(f;\Omega,\phi)\}, \quad (6)$$

where $\Re$ denotes the real part of its argument, * denotes the complex conjugate, ω and Ω the velocity (Rate) and spectral density (Scale) parameters of the filters, respectively, and θ and φ are characteristic phases that determine the degree of asymmetry along time and frequency axes, respectively. Equations (5) and (6) are consistent with physiological findings that most STRFs in the primary auditory cortex exhibit a quadrant separability property. Functions $H_{rate}$ and $H_{scale}$ are analytic signals (a signal which has no negative frequency components) obtained from $h_{rate}$ and $h_{scale}$ by, $$H_{rate}(t;\omega,\theta)=h_{rate}(t;\omega,\theta)+j\hat{h}_{rate}(t;\omega,\theta) \quad (7)$$

$$H_{scale}(f;\Omega,\phi)=h_{scale}(f;\Omega,\phi)+j\hat{h}_{scale}(f;\Omega,\phi), \quad (8)$$

where $\hat{\circ}$ denotes a Hilbert transformation. The terms $h_{rate}$ and $h_{scale}$ are temporal and spectral impulse responses, respectively, defined by sinusoidally interpolating between symmetric seed functions $h_r(\circ)$ (second derivative of a Gaussian function) and $h_s(\circ)$ (Gamma function), and their symmetric Hilbert transforms:

$$h_{rate}(t;\omega,\theta)=h_r(t;\omega)\cos\theta+\hat{h}_r(t;\omega)\sin\theta \quad (9)$$

$$h_{scale}(f;\Omega,\phi)=h_s(f;\Omega)\cos\phi+\hat{h}_s(f;\Omega)\sin\theta. \quad (10)$$

The impulse responses for different scales and rates are given by dilation $$h_r(t;\omega)=\omega h_r(\omega t) \quad (11)$$

$$h_s(f;\Omega)=\Omega h_s(\Omega f) \quad (12)$$

Therefore, the spectro-temporal response for an input spectrogram y(t,f) is given by $$r_+(t,f;\omega,\Omega;\theta,\phi)=y(t,f)*_{t,f}STRF_+(t,f;\omega,\Omega;\theta,\phi) \quad (13)$$

$$r_-(t,f;\omega,\Omega;\theta,\phi)=y(t,f)*_{t,f}STRF_-(t,f;\omega,\Omega;\theta,\phi) \quad (14)$$

where $*_{t,f}$ denotes convolution with respect to both time and frequency.

In certain embodiments of the invention, the spectro-temporal response $r_\pm(\cdot)$ is computed in terms of the output magnitude and phase of the downward (+) and upward (−) selective filters. To achieve this, the temporal and spatial filters, $h_{rate}$ and $h_{scale}$, respectively, can be equivalently expressed in the wavelet-based analytical forms $h_{rw}(\cdot)$ and $h_{sw}(\cdot)$ as:

$$h_{rw}(t;\omega)=h_r(t;\omega)+j\hat{h}_r(t;\omega) \quad (15)$$

$$h_{sw}(f;\Omega)=h_s(f;\Omega)+j\hat{h}_s(f;\Omega) \quad (16)$$

The complex responses to downward and upward selective filters, $z_+(\cdot)$ and $z_-(\cdot)$, respectively, are then defined as:

$$z_+(t,f;\Omega,\omega)=y(t,f)*_{t,f}[h^*_{rw}(t;\omega)h_{sw}(f;\Omega)] \quad (17)$$

$$z_-(t,f;\Omega,\omega)=y(t,f)*_{t,f}[h^*_{rw}(t;\omega)h_{sw}(f;\Omega)]. \quad (18)$$

The cortical response (Equations (13) and (14)) for all characteristic phases θ and φ can be easily obtained from $z_+(\cdot)$ and $z_-(\cdot)$ as follows:

$$r_+(t,f;\omega,\Omega;\theta,\phi)=|z_+|\cos(\angle z_+-\theta-\phi) \quad (19)$$

$$r_-(t,f;\omega,\Omega;\theta,\phi)=|z_-|\cos(\angle z_--\theta-\phi) \quad (20)$$

where $|\cdot|$ denotes the magnitude and $\angle\cdot$ denotes the phase. The magnitude and the phase of $z_+$ and $z_-$ have a physical interpretation: at any time t and for all the STRF's tuned to the same $(f,\omega,\Omega)$, those with $$\theta=\frac{1}{2}(\angle z_+ + \angle z_-) \text{ and } \phi=\frac{1}{2}(\angle z_+ - \angle z_-)$$

symmetries have the maximal downward and upward responses of $|z_+|$ and $|z_-|$. These maximal responses are utilized in certain embodiments of the invention for purposes of sound classification. Where the spectro-temporal modulation content of the spectrogram is of particular interest, the output 320 from the filters 310 having identical modulation selectivity or STRF's are summed to generate rate-scale fields 332, 334:

$$u_+(\omega,\Omega)=\sum_t\sum_f|z_+(t,f;\omega,\Omega)| \quad (21)$$

$$u_-(\omega,\Omega)=\sum_t\sum_f|z_-(t,f;\omega,\Omega)| \quad (22)$$

The data that emerges from the cortical model 104 consists of continuously updated estimates of the spectral and temporal modulation content of the auditory spectrogram 260. The parameters of the auditory model implemented by the present invention are derived from physiological data in animals and psychoacoustical data in human subjects.

Unlike conventional features used in sound classification, the auditory based features of the present invention have multiple scales of time and spectral resolution. Certain features respond to fast changes in the audio signal while others are tuned to slower modulation patterns. A subset of the features is selective to broadband spectra, and others are more narrowly tuned. In certain speech applications, for example, temporal filters (Rate) may range from 1 to 32 Hz, and spectral filters (Scale) may range from 0.5 to 8.00 Cycle/Octave to provide adequate representation of the spectro-temporal modulations of the sound.

In typical digitally implemented applications, the output of auditory model 105 is a multidimensional array in which modulations are represented along the four dimensions of time, frequency, rate and scale. In certain embodiments of the present invention, the time axis is averaged over a given time window, which results in a three mode tensor for each time window with each element representing the overall modulations at corresponding frequency, rate and scale. In order to obtain high resolution, which may be necessary in certain applications, a sufficient number of filters in each mode must be implemented. As a consequence, the dimensions of the feature space may be very large. For example, implementing 5 scale filters, 12 rate filters, and 128 frequency channels, the resulting feature space is 5×12×128=7680. Working in this feature space directly is impractical because of the sizable number of training samples required to adequately characterize the feature space.

Traditional dimensionality reduction methods like principal component analysis (PCA) are inefficient for multidimensional data because they treat all of the elements of the feature space without consideration of the varying degrees of redundancy and discriminative contribution of each mode. However, it is possible using multidimensional PCA to tailor the amount of reduction in each subspace independently of others based on the relative magnitude of corresponding singular values. Furthermore, it is also feasible to reduce the amount of training samples and computational load significantly since each subspace is considered separately. To achieve adequate data reduction for purposes of efficient sound classification, certain embodiments of the invention implement a generalized method for the PCA of multidimensional data based on higher-order singular-value decomposition (HOSVD).

As is well known, multilinear algebra is the algebra of tensors. Tensors are generalizations of scalars (no indices), vectors (single index), and matrices (two indices) to an arbitrary number of indices, which provide a natural way of representing information along many dimensions. A tensor $A \in R^{I_1\times I_2\times\ldots\times I_N}$ is a multi-index array of numerical values whose elements are denoted by $\alpha_{i_1 i_2 \ldots i_N}$. Matrix column vectors are referred to as mode-1 vectors and row vectors as mode-2 vectors. The mode-n vectors of an Nth order tensor A are the vectors with $I_n$ components obtained from A by varying index $I_n$ while keeping the other indices fixed. Matrix representation of a tensor is obtained by stacking all the columns (or rows or higher dimensional structures) of the tensor one after the other. The mode-n matrix unfolding of $A \in R^{I_1\times I_2\times\ldots\times I_N}$ denoted by $A_{(n)}$ is the $(I_n\times I_1 I_2\ldots I_{n-1}I_{n+1}\ldots I_N)$ matrix whose columns are n-mode vectors of tensor A An Nth-order tensor A has rank-1 when it is expressible as the outer product of N vectors:

$$A=U_1\circ U_2\circ\ldots\circ U_N. \quad (23)$$

The rank of an arbitrary Nth-order tensor A, denoted by r=rank (A) is the minimal number of rank-1 tensors that yield A in a linear combination. The n-rank of $A \in R^{I_1\times I_2\times\ldots\times I_N}$ denoted by $r_N$ is defined as the dimension of the vector space generated by the mode-n vectors $$R_n=\text{rank}_n(A)=\text{rank}(A_{(n)}). \quad (24)$$

The n-mode product of a tensor $A \in R^{I_1\times I_2\times\ldots\times I_N}$ by a matrix $U \in R^{J_n\times I_n}$, denoted by $A\times_n U$, is an $(I_1\times I_2\times\ldots\times J_n\times\ldots\times I_N)$-tensor given by $$(A\times_n U)_{i_1 i_2\ldots j_n\ldots i_N}=\sum_{i_n}a_{i_1 i_2\ldots i_n\ldots i_N}u_{j_n i_n} \quad (25)$$

for all index values.

As is known in the art, matrix Singular-Value Decomposition (SVD) orthogonalizes the space spanned by column and rows of a matrix. In general, every matrix D can be written as the product $$D=U\cdot S\cdot V^T=S\times_1 U\times_2 V \quad (26)$$

in which U and V are unitary matrices containing the left- and right-singular vectors of D. S is a pseudo-diagonal matrix with ordered singular values of D on the diagonal.

If D is a data matrix in which each column represents a data sample, then the left singular vectors of D (matrix U) are the principal axes of the data space. In certain embodiments of the invention, only the coefficients corresponding to the largest singular values of D (Principal Components or PCs) are retained so as to provide an effective means for approximating the data in a low-dimensional subspace. To generalize this concept to multidimensional data often used in the present invention, a generalization of SVD to tensors may be implemented. As is known in the art, every $(I_1 \times I_2 \times \ldots \times I_N)$-tensor A can be written as the product $$A = S \times_1 U^{(1)} \times_2 U^{(2)} \ldots \times_N U^{(N)} \tag{27}$$

in which $U^{(n)}$ is a unitary matrix containing left singular vectors of the mode-n unfolding of tensor A, and S is a $(I_1 \times I_2 \times \ldots \times I_N)$ tensor having the properties of all-orthogonality and ordering. The matrix representation of the HOSVD can be written as $$A_{(n)} = U^{(n)} \cdot S_{(n)} \cdot (U^{(n+1)} \otimes \ldots \otimes U^{(N)} \otimes U^{(1)} \otimes U^{(2)} \otimes \ldots \otimes U^{(n-1)})^T \tag{28}$$

where $\otimes$ denotes the Kronecker product. Equation (28) can also be written as:

$$A_{(n)} = U^{(n)} \cdot \Sigma^{(n)} \cdot V^{(n)^T} \tag{29}$$

in which $\Sigma^{(n)}$ is a diagonal matrix made by singular values of $A^{(n)}$ and $$V^{(n)} = (U^{(n+1)} \otimes \ldots \otimes U^{(N)} \otimes U^{(1)} \otimes U^{(2)} \otimes \ldots U^{(n-1)}). \tag{30}$$

It has been shown that the left-singular matrices of the matrix unfolding of A corresponds to unitary transformations that induce the HOSVD structure, which in turn ensures that the HOSVD inherits all the classical space properties from the matrix SVD.

HOSVD results in a new ordered orthogonal basis for representation of the data in subspaces spanned by each mode of the tensor. Dimensionality reduction in each space may be obtained by projecting data samples on principal axes and keeping only the components that correspond to the largest singular values of that subspace. However, unlike the matrix case in which the best rank-R approximation of a given matrix is obtained from the truncated SVD, this procedure does not result in optimal approximation in the case of tensors. Instead, the optimal best rank-$(R_1, R_2, \ldots R_N)$ approximation of a tensor can be obtained by an iterative algorithm in which HOSVD provides the initial values, such as is described in De Lathauwer, et al., *On the Best Rank-*1 *and Rank-*$(R_1, R_2, \ldots, R_N)$ *Approximation of Higher Order Tensors, SIAM Journal of Matrix Analysis and Applications, Vol.* 24, *No.* 4, 2000.

The auditory model transforms a sound signal to its corresponding time-varying cortical representation. Averaging over a given time window results in a cube of data 320 in rate-scale-frequency space. Although the dimension of this space is large, its elements are highly correlated making it possible to reduce the dimension significantly using a comprehensive data set, and finding new multilinear and mutually orthogonal principal axes that approximate the real space spanned by these data. The resulting data tensor D, obtained by stacking a comprehensive set of training tensors, is decomposed to its mode-n singular vectors:

$$D = S \times_1 U_{frequency} \times_2 U_{rate} \times_3 U_{scale} \times_4 U_{samples} \tag{31}$$

in which $U_{frequency}$, $U_{rate}$ and $U_{scale}$ are orthonormal ordered matrices containing subspace singular vectors, obtained by unfolding D along its corresponding modes. Tensor S is the core tensor with the same dimensions as D.

Figure 4:
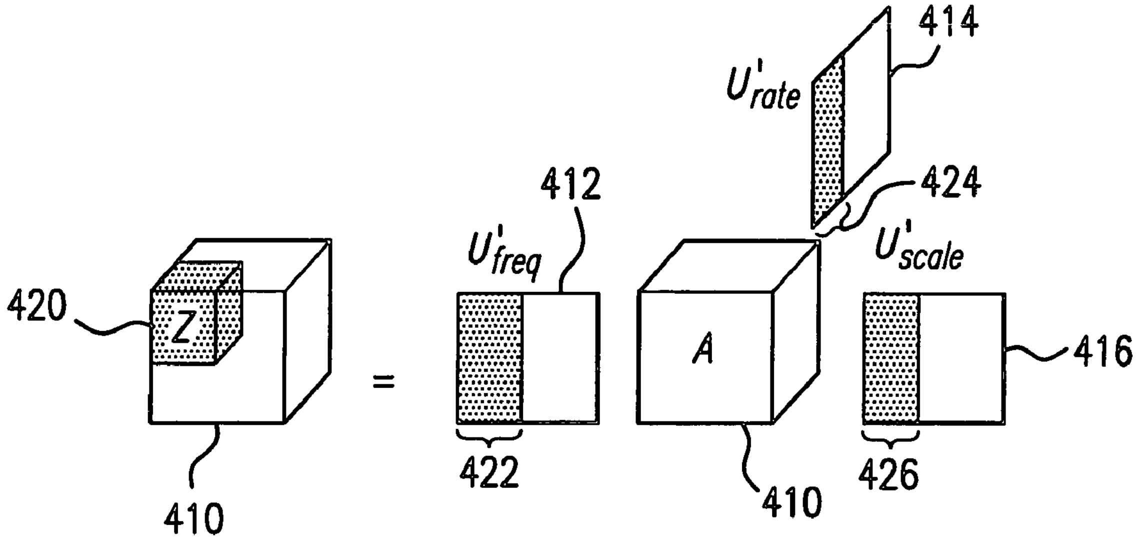
FIG. 4 is an illustration of an exemplary multilinear dimensionality reduction implementation of the present invention.

Referring to FIG. 4, each singular matrix is truncated by, for example, setting a predetermined threshold so as retain only the desired number of principal axes in each mode. New sound samples from live data, i.e., subsequent to the training phase, are first transformed to their cortical representation, A, indicated at 410, and are then projected onto the truncated orthonormal axes $U'_{freq}$, $U'_{rate}$, and $U'_{scale}$:

$$Z = A \times_1 U'^T_{freq} \times_2 U'^T_{rate} \times_3 U'^T_{scale} \tag{32}$$

The resulting tensor Z, indicated at 420, whose dimension is equal to the total number of retained singular vectors 422, 424 and 426, in each mode 412, 414, and 416, respectively, contains the multilinear cortical principal components of the sound sample. In certain embodiments of the invention, Z is then vectorized and normalized by subtracting its mean and dividing by its norm to obtain a compact feature vector for classification.

Referring once again to FIG. 1, the feature data set processed by multilinear analyzer 106 is presented to classifier 108. The reduction in the dimensions of the feature space in accordance with the present invention allow the use of a wide variety of classifiers known in the art. Through certain benefits of the present invention, the advantages of physiologically-based features may be implemented in conjunction with classifiers familiar to the skilled artisan. In certain embodiments of the invention, classification is performed using a Support Vector Machine (SVM) having a radial basis function as the kernel trained on the features of interest. SVMs, as is known in the art, find the optimal boundary that separates two classes in such a way as to maximize the margin between a separating boundary and closest samples thereto, i.e., the support vectors.

Figure 5:
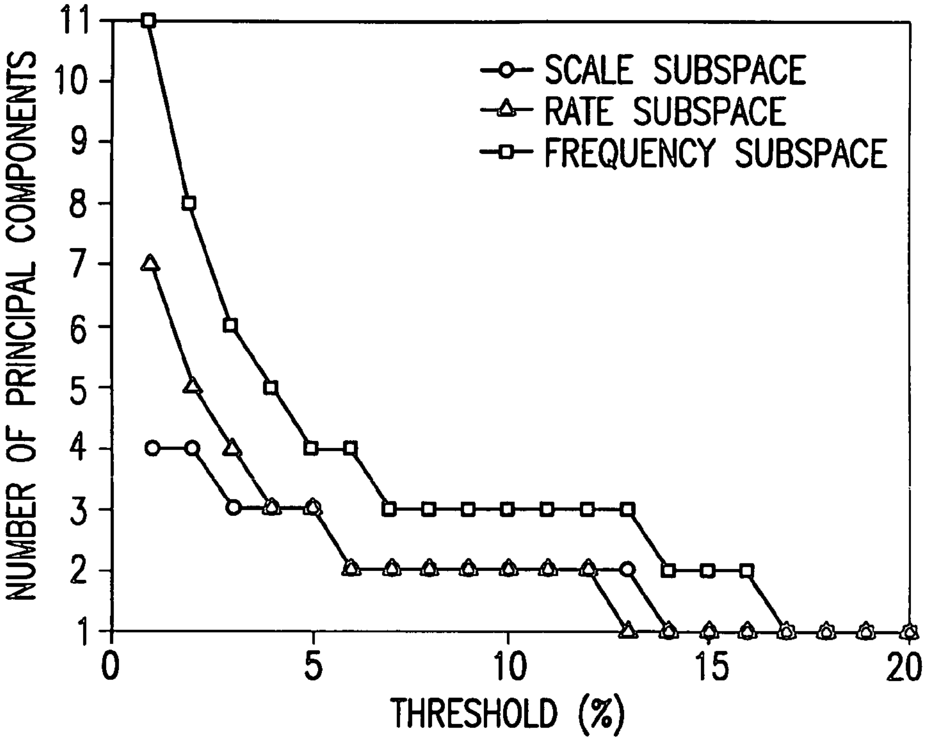
FIG. 5 is a graph illustrating the number of principal components of the cortical response to retain for classification as a function of a selection threshold defined as a percentage of the contribution of the principal component to the overall representation of the response.
Figure 6:
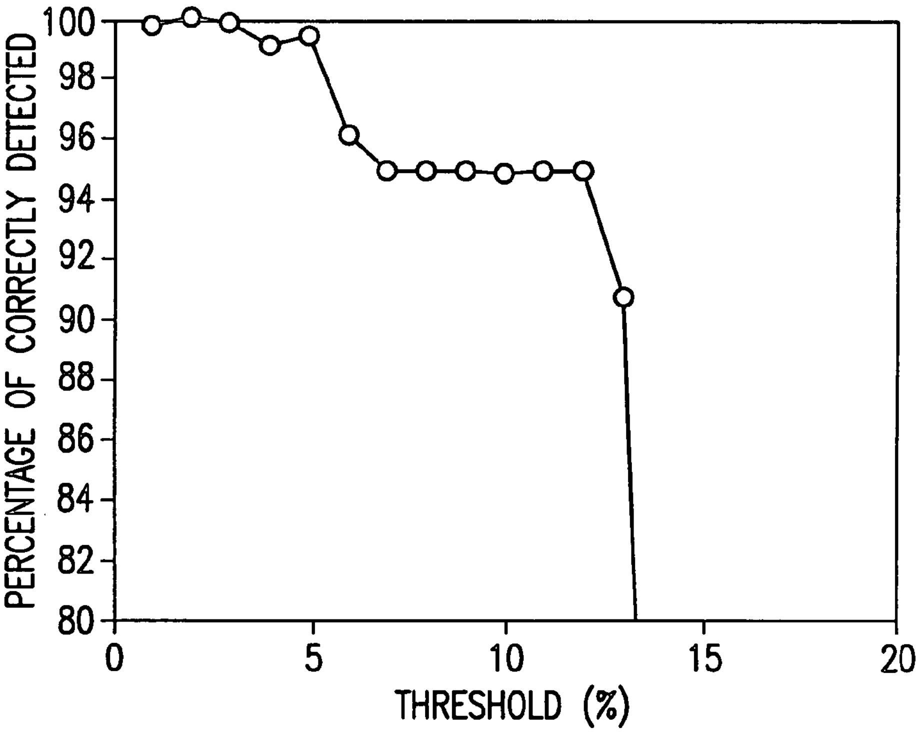
FIG. 6 is a graph illustrating the percentage of correctly classified acoustic features as a function of a selection threshold defined as a percentage of the contribution of the principal component to the overall representation of the response.

In accordance with certain aspects of the invention, the number of retained principal components (PCs) in each subspace is determined by analyzing the contribution of each PC to the representation of associated subspace. By one measure, the contribution of $j_{th}$ principal component of subspace $S_i$, whose corresponding eigenvalue is $\lambda_{i,j}$, may be computed as $$\alpha_{i,j} = \frac{\lambda_{i,j}}{\sum_{k=1}^{N_i} \lambda_{i,k}} \tag{33}$$

where $N_i$ denotes the dimension of $S_i$, which, in the exemplary configuration described above, is 128 for the frequency dimension, 12 for the rate dimension and 5 for the scale dimension. The number of PCs to retain in each subspace then can be specified per application. In certain embodiments of the invention, only those PCs are retained whose $\alpha$, as calculated by Equation (33) is larger than some predetermined threshold. FIG. 5 illustrates exemplary behavior of the number of principal components that are retained in each of the three subspaces as a function of threshold in percentage of total contribution. In FIG. 6, the classification accuracy is demonstrated as a function of the number of retained principal components. As shown in FIG. 6, to achieve 100% classification accuracy, the principle components to be retained is determined to be 7 for frequency, 5 for rate and 4 for scale subspaces, which, as seen in FIG. 5, requires the retention of PCs that have contribution of 3.5% or greater. Thus, to determine the truncation of the axes $U'_{freq}$, $U'_{rate}$, and $U'_{scale}$, the system training period would adjust the threshold, or equivalently, the number of retained PCs, until desired classification accuracy is established in the training data (as presumably the classification of the training data is known). The truncated signal size is then maintained when live data are to be classified.

To illustrate the capabilities of the invention, an exemplary embodiment thereof will be compared with two more elaborate systems. The first is proposed by Scheirer, et al., as described in *Construction and Evaluation of a Robust Multifeature Speech/Music Discriminator, International Conference on Acoustic, Speech and Signal Processing, Munich, Germany,* 1997 (hereinafter, the "Multifeature" system), in which thirteen features in time, frequency, and cepstrum domains are used to model speech and music. Several classification techniques (e.g., MAP, GMM, KNN) are then employed to achieve the intended performance level. The second system is a speech/non-speech segmentation technique proposed by Kingsbury, et al., *Robust Speech Recognition in Noisy Environments: The* 2001 *IBM SPINE Evaluation System, International Conference on Acoustic, Speech and Signal Processing, vol. I, Orlando, Fla., May* 2002 (hereinafter, the "Voicing-Energy" system), in which frame-by-frame maximum autocorrelation and log-energy features are measured, sorted and then followed by linear discriminant analysis and a diagonalization transform.

Figure 7:
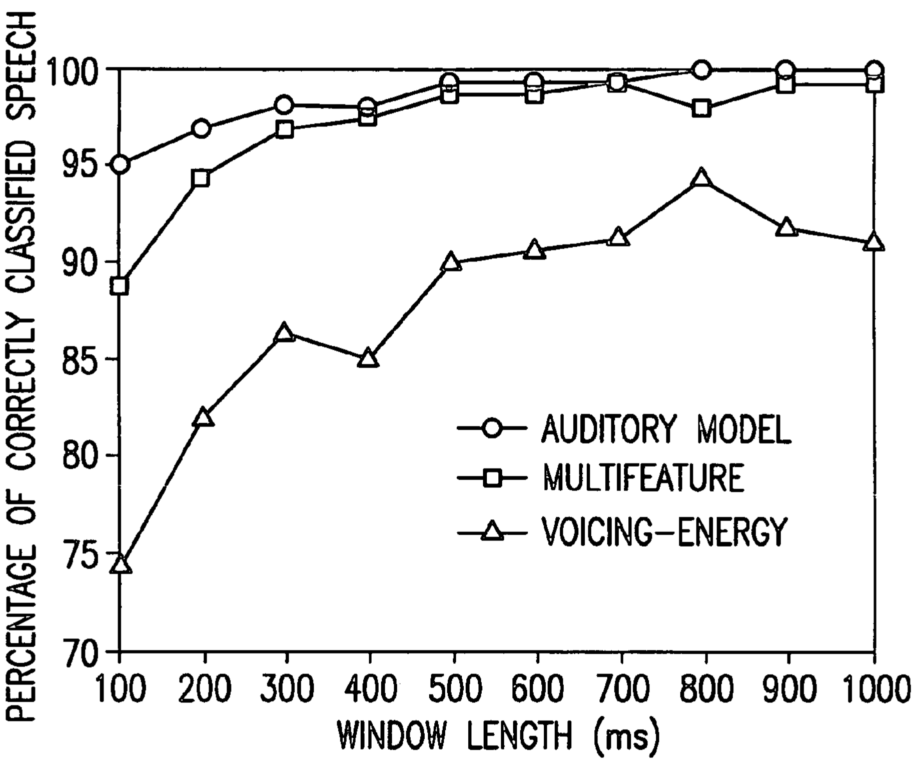
FIG. 7 is a graph of percentage of correctly classified speech features as a function of the time averaging window comparing the present invention with two systems of the prior art.
Figure 8:
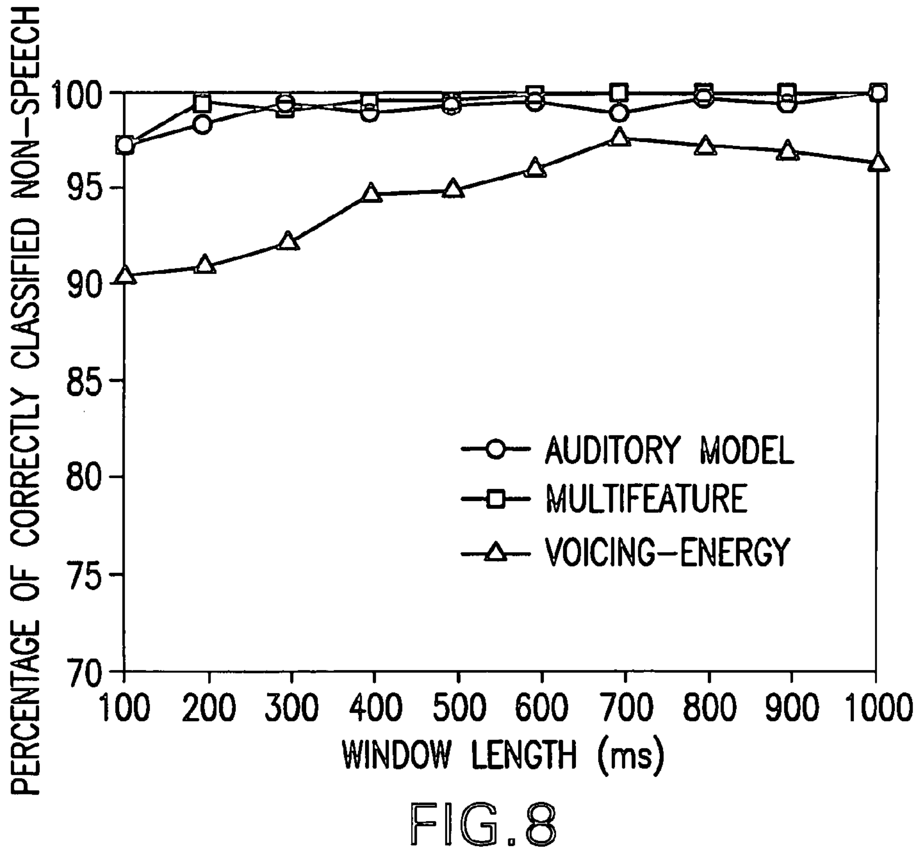
FIG. 8 is a graph of percentage of correctly classified non-speech features as a function of the time averaging window comparing the present invention with two systems of the prior art.

The auditory model of the present invention and the two benchmark algorithms from the prior art were trained and tested on the same database. One of the important parameters in any such speech detection/discrimination task is the time window or duration of the signal to be classified, because it directly affects the resolution and accuracy of the system. FIGS. 7 and 8 demonstrate the effect of window length on the percentage of correctly classified speech and non-speech. In all three methods, some features may not give a meaningful measurement when the time window is too short. The classification performance of the three systems for two window lengths of 1 second and 0.5 second is shown in Tables I and II. The accuracy of all three systems improves as the time window increases.

Percentage of Correct Classification for Window Length of One Second

TABLE I

| | Auditory Model | Multifeature | Voicing-Energy |
|---|---|---|---|
| Correct Speech | 100% | 99.3% | 91.2% |
| Correct Non-Speech | 100% | 100% | 96.3% |

Percentage of Correct Classification for Window Length of Half a Second

TABLE II

| | Auditory Model | Multifeature | Voicing-Energy |
|---|---|---|---|
| Correct Speech | 99.4% | 98.7% | 90.0% |
| Correct Non-Speech | 99.4% | 99.5% | 94.9% |

Percentage of Correct Classification for Window Length of Half a Second

Audio processing systems designed for realistic applications must be robust in a variety of conditions because training the systems for all possible situations is impractical. Detection of speech at very low SNR is desired in many applications such as speech enhancement in which a robust detection of non-speech (noise) frames is crucial for accurate measurement of the noise statistics. A series of tests were conducted to evaluate the generalization of the three methods to unseen noisy and reverberant sound. Classifiers were trained solely to discriminate clean speech from non-speech and then tested in three conditions in which speech was distorted with noise or reverberation. In each test, the percentage of correctly detected speech and non-speech was considered as the measure of performance. For the first two tests, white and pink noise were added to speech with specified signal to noise ratio (SNR). White and pink noise were not included as non-speech samples in the training data set. SNR was measured using:

$$SNR = 10\log\frac{Ps}{Pn}, \qquad (34)$$

where Ps and Pn are the average powers of speech and noise, respectively.

Figure 9:
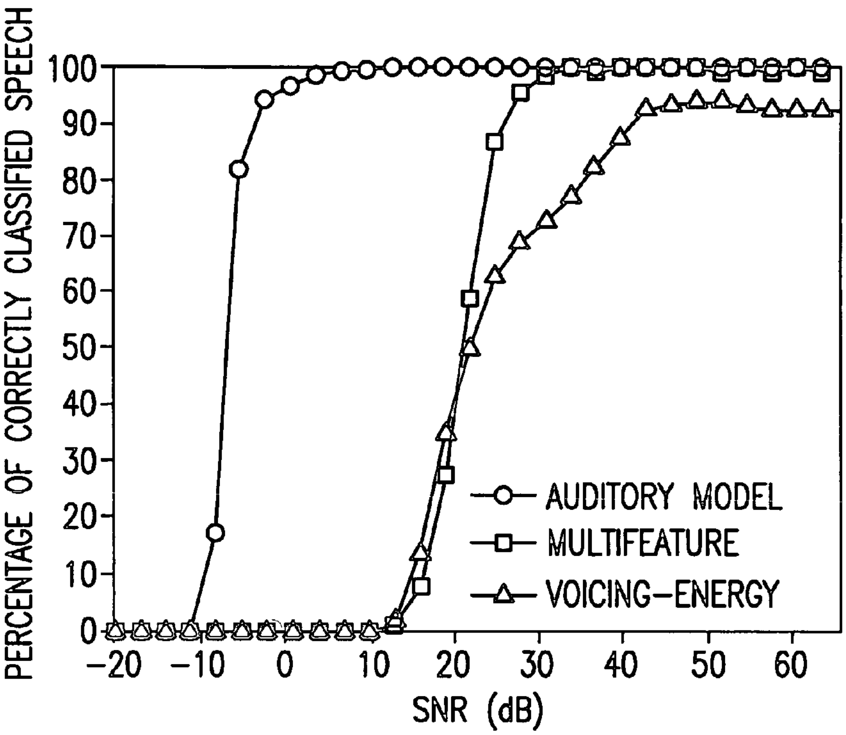
FIG. 9 is a graph of percentage of correctly classified speech features as a function of signal-to-noise ratio (additive white noise) comparing the present invention with two systems of the prior art.
Figure 10:
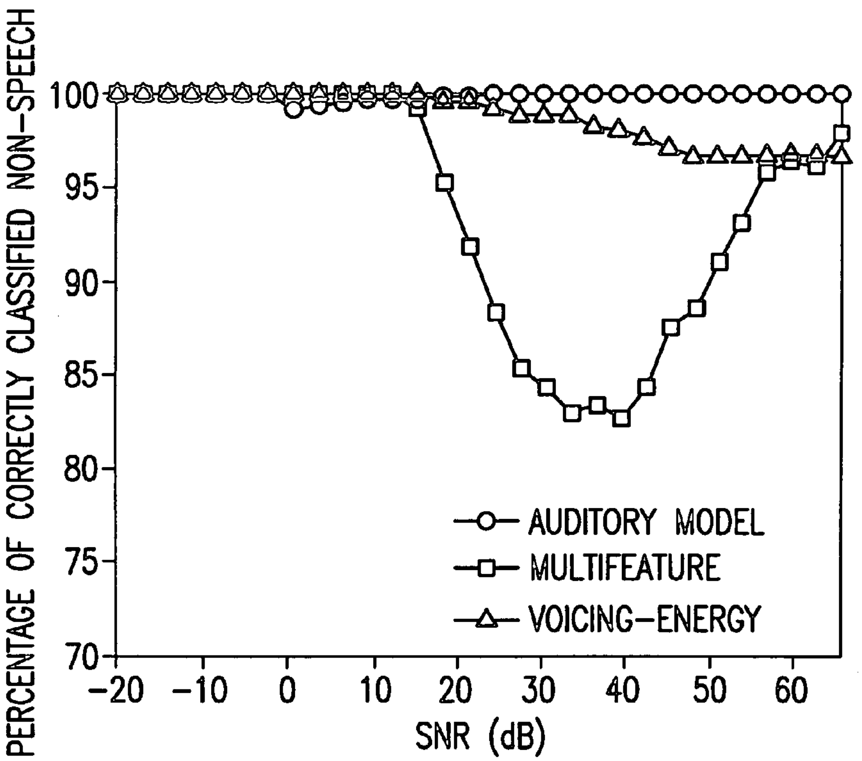
FIG. 10 is a graph of percentage of correctly classified non-speech features as a function of signal-to-noise ratio (additive white noise) comparing the present invention with two systems of the prior art.
Figure 11:
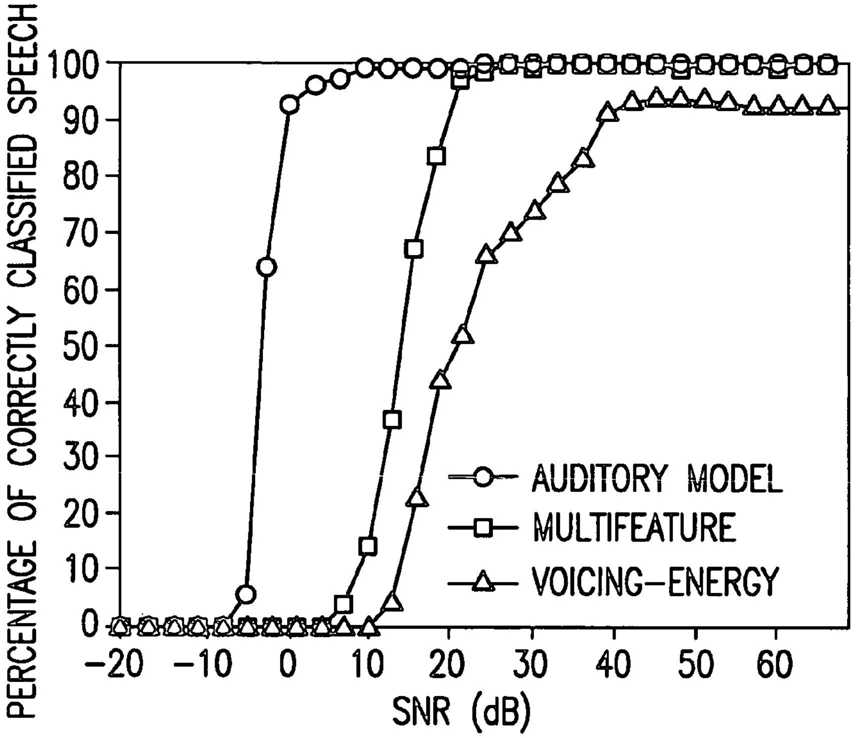
FIG. 11 is a graph of percentage of correctly classified speech features as a function of signal-to-noise ratio (additive pink noise) comparing the present invention with two systems of the prior art.
Figure 12:
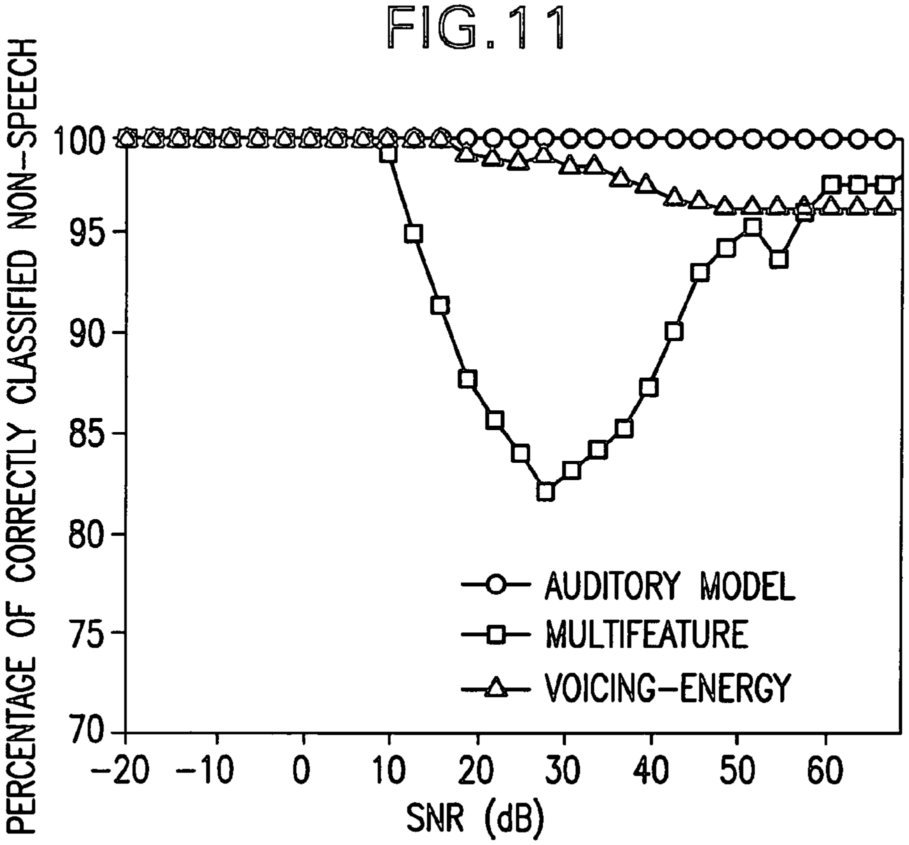
FIG. 12 is a graph of percentage of correctly classified non-speech features as a function of signal-to-noise ratio (additive pink noise) comparing the present invention with two systems of the prior art.
Figure 15:
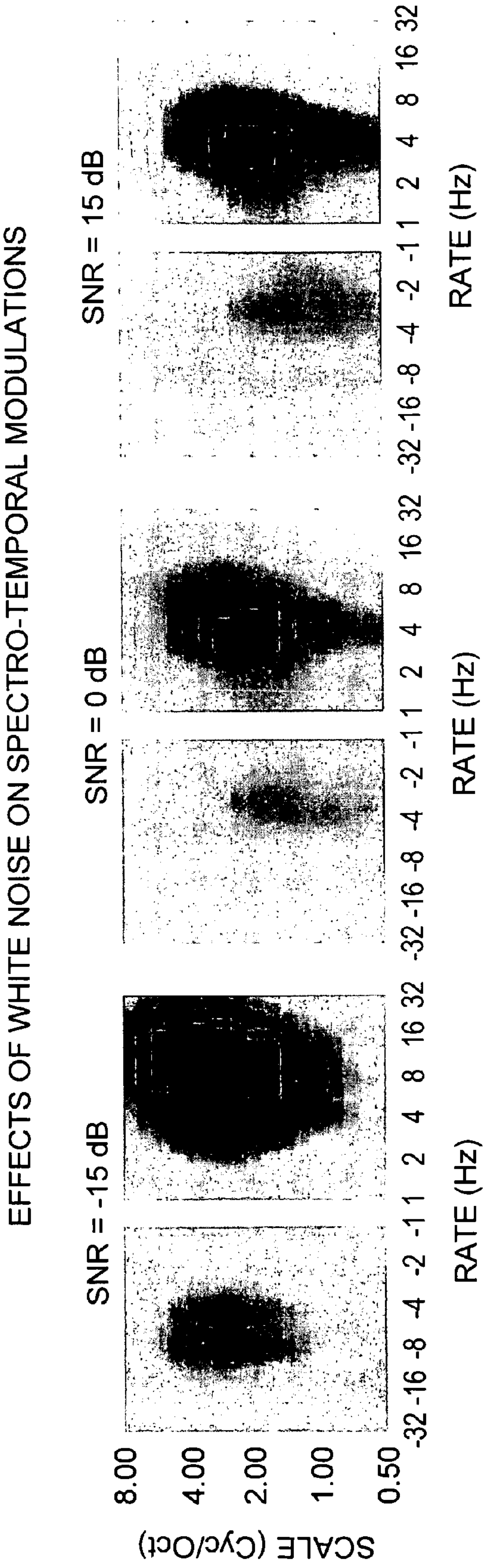
FIG. 15 is a spectro-temporal modulation plot produced in accordance with the present invention illustrating the effects of white noise thereon.
Figure 16:
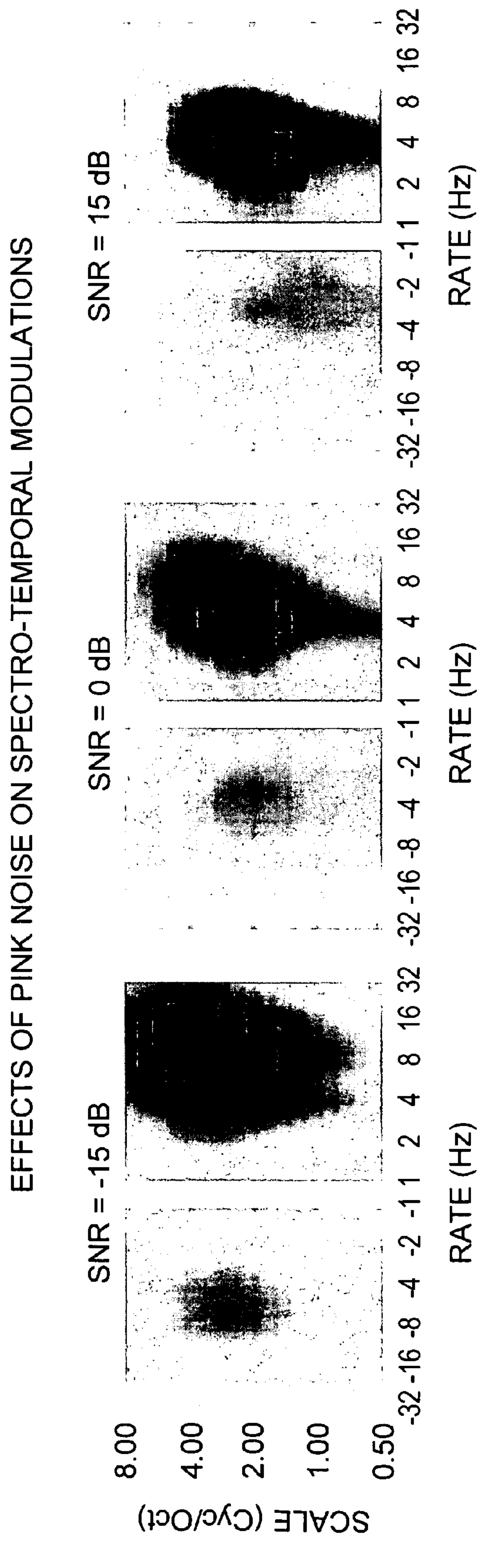
FIG. 16 is a spectro-temporal modulation plot produced in accordance with the present invention illustrating the effects of pink noise thereon.

FIGS. 15 and 16 illustrate the effect of white and pink noise on the average spectro-temporal modulations of speech. The spectro-temporal representation of noisy speech preserves the speech specific features (e.g. near 4 Hz, 2 Cyc/Oct) even at SNR as low as 0 dB (FIGS. 15 and 16, middle). The detection results for speech in white noise, as shown in FIGS. 9 and 10, demonstrate that while the three systems have comparable performance in clean conditions, the auditory features of the present invention remain robust down to fairly low SNRs. This performance is repeated with additive pink noise, although performance degradation for all systems occurs at higher SNRs, as shown in FIGS. 11 and 12, because of more overlap between speech and noise energy.

Figure 13:
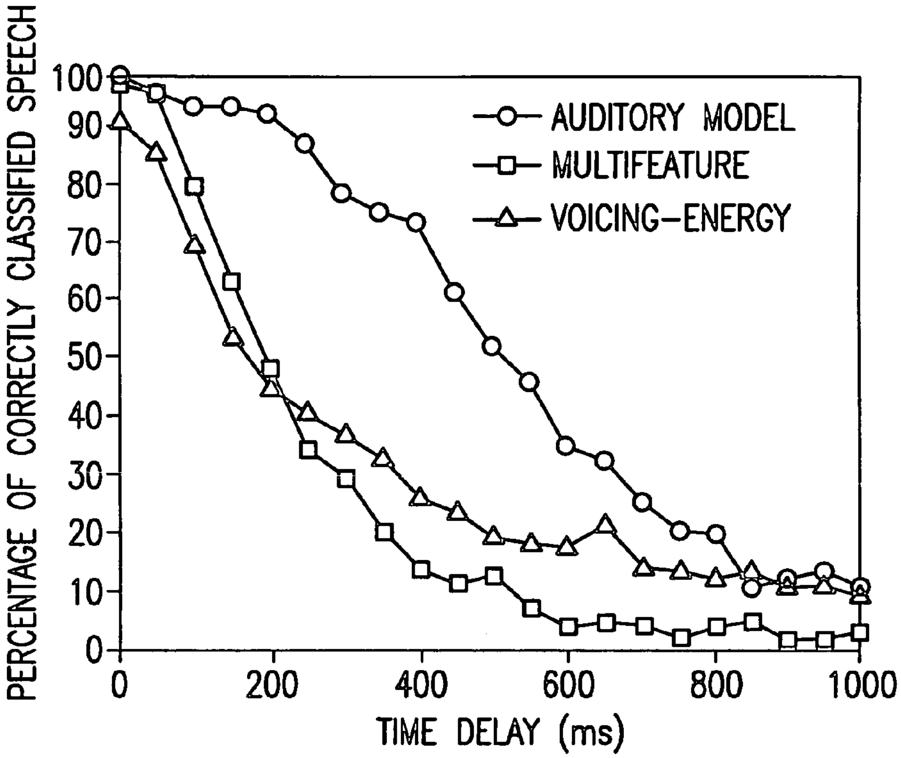
FIG. 13 is a graph of percentage of correctly classified speech features as a function of time delay of reverberation comparing the present invention with two systems of the prior art.
Figure 14:
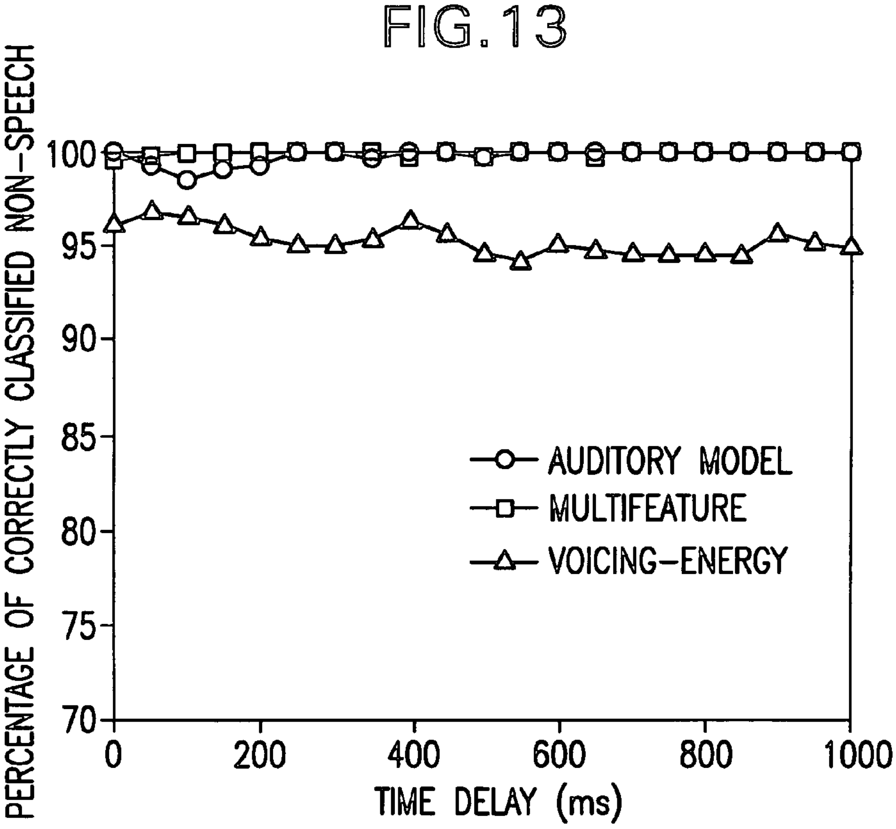
FIG. 14 is a graph of percentage of correctly classified non-speech features as a function of time delay of reverberation comparing the present invention with two systems of the prior art.
Figure 17:
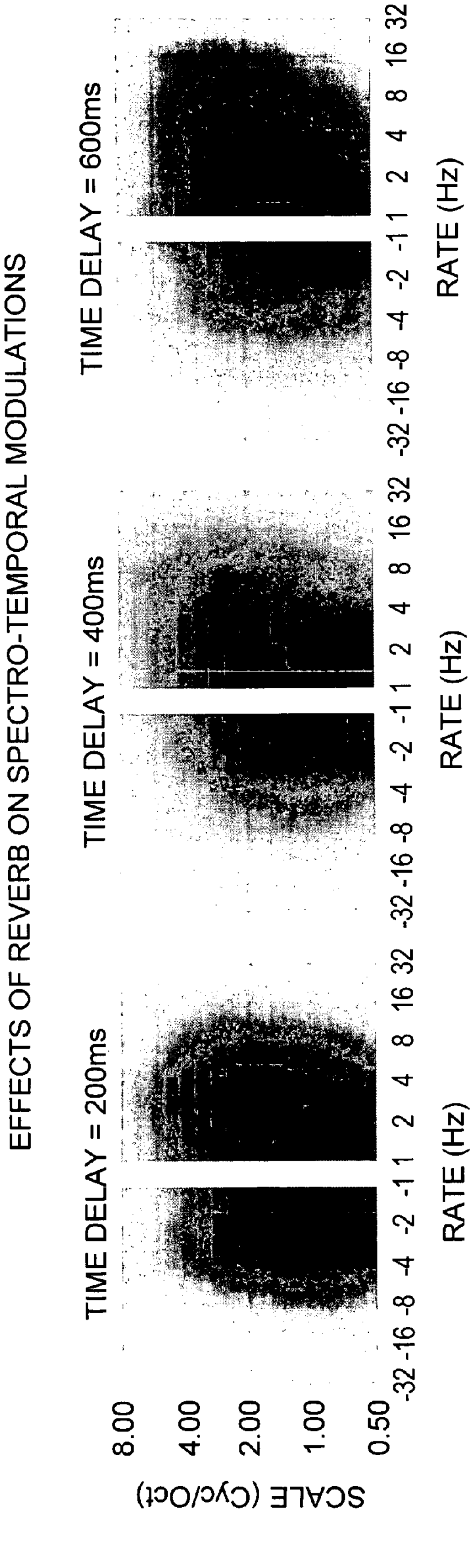
FIG. 17 is a spectro-temporal modulation plot produced in accordance with the present invention illustrating the effects of reverberation thereon.

Reverberation is another widely encountered distortion in realistic applications. To examine the effect of different levels of reverberation on the performance of these systems, a realistic reverberation condition was simulated by convolving the signal with a random Gaussian noise with exponential decay. The effect on the average spectro-temporal modulations of speech is shown in FIG. 17. Increasing the time delay results in gradual loss of high-rate temporal modulations of speech. FIGS. 13 and 14 demonstrate the effect of reverberation on the classification accuracy.

The descriptions above are intended to illustrate possible implementations of the present invention and are not restrictive. Many variations, modifications and alternatives will become apparent to the skilled artisan upon review of this disclosure. For example, components equivalent to those shown and described may be substituted therefor, elements and methods individually described may be combined, and elements described as discrete may be distributed across many components. The scope of the invention should therefore be determined with reference to the appended claims, along with their full range of equivalents.

What is claimed is:

1. A method for discriminating sounds in an audio signal comprising the steps of:

forming an auditory spectrogram from the audio signal, said auditory spectrogram characterizing a physiological response to sound represented by the audio signal;

establishing a plurality of modulation-selective filters tuned to a range of frequency and temporal modulations of said auditory spectrogram;

filtering said auditory spectrogram into a plurality of multidimensional, time-varying cortical response signals, each of said cortical response signals indicative of the frequency modulations of said auditory spectrogram over a corresponding predetermined range of scales and of the temporal modulations of said auditory spectrogram over a corresponding predetermined range of rates;

decomposing said cortical response signals into orthogonal multidimensional component signals; said cortical response signals existing in a cubic representation of rate, scale, and frequency components prior to the step of decompositiom; said orthogonal multidimensional component signals including multiple scales of time and spectral resolution;

truncating said orthogonal multidimensional component signals; and classifying said truncated component signals to discriminate therefrom a signal corresponding to a predetermined sound.

2. The method for discriminating sounds in an audio signal as recited in claim 1, where said filtering step includes the step of convolving in both requisite time and requisite frequency said auditory spectrogram with each of a plurality of spectro-temporal response fields.

3. The method for discriminating sounds in an audio signal as recited in claim 2, where said filtering step further includes the step of providing a corresponding wavelet as said each spectro-temporal response fields.

4. The method for discriminating sounds in an audio signal as recited in claim 1 further including the step of averaging with respect to time over a predetermined number of time increments said cortical response signals prior to said decomposing step.

5. The method for discriminating sounds in an audio signal as recited in claim 4, where said decomposing step includes the step of decomposing said cortical response signals into orthogonal scale, rate and frequency components.

6. The method for discriminating sounds in an audio signal as recited in claim 1 further including the steps of:

forming a training auditory spectrogram from a known audio signal, said known audio signal associated with a corresponding known sound;

establishing a plurality of modulation-selective filters tuned to a range of frequency and temporal modulations of said training auditory spectrogram;

filtering said training auditory spectrogram into a plurality of multidimensional, time-varying training cortical response signals, each of said training cortical response signals indicative of the frequency modulations of said training auditory spectrogram over a corresponding predetermined range of scales and of the temporal modulations of said training auditory spectrogram over a corresponding predetermined range of rates;

decomposing said training cortical response signals into orthogonal multidimensional component training signals; said cortical response signals existing in a cubic representation of rate, scale, and frequency components prior to the step of decomposition; said orthogonal multidimensional component training signals including multiple scales of time and spectral resolution;

determining a signal size corresponding to each of said orthogonal multidimensional component training signals, said signal size setting a size of said corresponding orthogonal multidimensional component training signal to retain for classification;

truncating said orthogonal multidimensional component training signals to said signal size;

classifying said truncated orthogonal multidimensional component training signals;

comparing said classification of said truncated orthogonal multidimensional component training signals with a classification of said known sound; and increasing said signal size and repeating the method at said training signal truncating step if said classification of said truncated orthogonal multidimensional component training signals does not match said classification of said known sound to within a predetermined tolerance.

7. The method for discriminating sounds in an audio signal as recited in claim 6, where said signal size determining step includes the steps of:

establishing a contribution threshold;

determining a contribution to each said orthogonal component training signals by a corresponding signal component thereof;

selecting as said signal size a number of said corresponding signal components whose contribution to each said orthogonal component training signals is greater than said contribution threshold.

8. The method for discriminating sounds in an audio signal as recited in claim 6, where said orthogonal multidimensional component signal truncating step includes the step of truncating each of said orthogonal component signals to said corresponding signal size.

9. The method for discriminating sounds in an audio signal as recited in claim 1, where said classifying step includes the step of specifying human speech as said predetermined sound.

10. A method for discriminating sounds in an acoustic signal comprising the steps of:

providing a known audio signal associated with a known sound having a known sound classification;

forming a training auditory spectrogram from said known audio signal;

establishing a plurality of modulation-selective filters tuned to a range of frequency and temporal modulations of said training auditory spectrogram;

filtering said training auditory spectrogram into a plurality of multidimensional, time-varying training cortical response signals, each of said training cortical response signals indicative of the frequency modulations of said training auditory spectrogram over a corresponding predetermined range of scales and of the temporal modulations of said training auditory spectrogram over a corresponding predetermined range of rates;

decomposing said training cortical response signals into orthogonal multidimensional component training signals; said training cortical response signals existing in a cubic representation of rate, scale, and frequency components prior to the step of decomposition; said orthogonal multidimensional component training signals including multiple scales of time and spectral resolution;

determining a signal size corresponding to each of said orthogonal multidimensional component training signals, said signal size setting a size of said corresponding orthogonal multidimensional component training signal to retain for classification;

truncating said orthogonal multidimensional component training signals to said signal size;

classifying said truncated orthogonal multidimensional component training signals;

comparing said classification of said truncated orthogonal multidimensional component training signals with a classification of said known sound;

increasing said signal size and repeating the method at said training signal truncating step if said classification of said truncated orthogonal multidimensional component training signals does not match said classification of said known sound to within a predetermined tolerance;

converting the acoustic signal to an audio signal;

forming an auditory spectrogram from said audio signal, said auditory spectrogram characterizing a physiological response to sound represented by the audio signal;

establishing a plurality of modulation-selective filters tuned to a range of frequency and temporal modulations of said auditory spectrogram;

filtering said auditory spectrogram into a plurality of multidimensional, time-varying cortical response signals, each of said cortical response signals indicative of the frequency modulations of said auditory spectrogram over a corresponding predetermined range of scales and the temporal modulations of said auditory spectrogram over a corresponding predetermined range of rates;

decomposing said cortical response signals into orthogonal multidimensional component signals; said cortical response signals existing in a cubic representation of rate, scale, and frequency components prior to the step of decomposition; said orthogonal multidimensional component signals including multiple scales of time and spectral resolution;

truncating said orthogonal multidimensional component signals to said signal size; and classifying said truncated component signals to discriminate therefrom a signal corresponding to a predetermined sound.

11. The method for discriminating sounds in an acoustic signal as recited in claim 10, where said training auditory spectrogram filtering step and said auditory spectrogram filtering step both include the step of filtering via directional selective filters said auditory spectrogram into directional components of said plurality of multidimensional cortical response signals.

12. The method for discriminating sounds in an acoustic signal as recited in claim 11, where said training auditory spectrogram filtering step and said auditory spectrogram filtering step both include the step of selecting maximally directed cortical response signals as said plurality of multidimensional cortical response signals.

13. The method for discriminating sounds in an acoustic signal as recited in claim 11, where said training auditory spectrogram filtering step and said auditory spectrogram filtering step both include the step providing downward selective filters and upward selective filters as said directional selective filters.

14. The method for discriminating sounds in an acoustic signal as recited in claim 10, where said classifying step includes the step of specifying human speech as said predetermined sound.

15. A system to discriminate sounds in an acoustic signal comprising:

an early auditory model execution unit operable to produce at an output thereof an auditory spectrogram of an audio signal provided as an input thereto, said audio signal being a representation of said acoustic signal;

a cortical model execution unit coupled to said output of said auditory model execution unit so as to receive said auditory spectrogram and to produce therefrom at an output thereof a time-varying signal representative of a cortical response to the acoustic signal; said cortical response signal existing in a cubic representation of rate, scale, and frequency components;

a multi-linear analyzer coupled to said output of said cortical model execution unit and operable to determine a set of multidimensional orthogonal axes from said cortical representations, said multi-linear analyzer further operable to produce a reduced data set relative to said set of multidimensional orthogonal axes; and a classifier for determining speech from said reduced data set.

16. The system for discriminating sounds in an acoustic signal as recited in claim 15, wherein said cortical model execution unit includes a bank of spectro-temporal modulation selective filters.

17. The system for discriminating sounds in an acoustic signal as recited in claim 16, wherein said each of said spectro-temporal modulation selective filters is characterized by a wavelet.

18. The system for discriminating sounds in an acoustic signal as recited in claim 16, wherein said each of said spectro-temporal modulation selective filters is directionally selective.

19. The system for discriminating sounds in an acoustic signal as recited in claim 15, wherein said classifier includes at least one support vector machine.

20. The system for discriminating sounds in an acoustic signal as recited in claim 15, where said classifier is operable to discriminate human speech.

* * * * *